United States Patent
Budtz (12)

(10) Patent No.: US 6,258,390 B1
(45) Date of Patent: Jul. 10, 2001

(54) PROCESS FOR MAKING CHEESE

(75) Inventor: Peter Budtz, Frederiksberg (DK)

(73) Assignee: Novozymes A/S Patents, Bagsvaerd (DK)

(*) Notice: Subject to any disclaimer, the term of this patent is extended or adjusted under 35 U.S.C. 154(b) by 0 days.

(21) Appl. No.: 08/990,884

(22) Filed: Dec. 15, 1997

Related U.S. Application Data

(63) Continuation of application No. PCT/DK96/00279, filed on Jun. 25, 1996.

(30) Foreign Application Priority Data

Jun. 30, 1995 (DK) .................................................. 0764/95
Jun. 25, 1996 (WO) .................................. PCT/DK96/00279

(51) Int. Cl.$^7$ ...................................................... A23C 9/12
(52) U.S. Cl. ................................ 426/36; 426/34; 426/38; 426/39; 426/582
(58) Field of Search ............................... 426/34, 36, 38, 426/39, 40, 42, 43, 52, 580, 582

(56) References Cited

U.S. PATENT DOCUMENTS 5,681,598 * 10/1997 Kuraishi et al. ...................... 426/36

FOREIGN PATENT DOCUMENTS

| 0 711 504 | 5/1996 | (EP) . |
| 93/22930 | 11/1993 | (WO) . |
| 94/21130 | 9/1994 | (WO) . |

* cited by examiner

*Primary Examiner*—Leslie Wong
(74) *Attorney, Agent, or Firm*—Elias Lambiris Esq.

(57) ABSTRACT

A process for making cheese including: a) adding to cheesemilk a transglutaminase, incubating for a suitable period, b) incubating with a rennet so as to cause clotting, and c) separating whey from the coagulate, and d) processing the coagulate into cheese. Cheese products produced by said process are contemplated and to the use of transglutaminase for maintaining proteins in the cheese material during a conventional cheese-making process.

18 Claims, No Drawings

PROCESS FOR MAKING CHEESE

CROSS-REFERENCE TO RELATED APPLICATIONS

This application is a continuation of PCT/DK96/00279 filed Jun. 25, 1996 and claims priority under 35 U.S.C. 119 of Danish application Ser. No. 0764/95 filed Jun. 30, 1995, the contents of which are fully incorporated herein by reference.

FIELD OF THE INVENTION

The present invention relates to a process for making cheese in improved yields by the use of a transglutaminase, and further cheese products produced by said process.

The invention is also directed towards the use of transglutaminase for maintaining proteins in the cheese material during a cheese-making process.

BACKGROUND OF THE INVENTION

The ability of ruminants to convert grass and other plant materials, being indigestible to man, into valuable nutritious matter, such as milk and meat, has for thousands of years been essential for the existence of a great many people all over the world.

Man has made butter and cheese from milk for many years. Originally cheese-making served as a method for preserving excess milk in the summer.

The industrial manufacturing of cheese started up more than 100 years ago, as the capability of handling large amounts of milk reached a sufficient technical stage and rennet became commercially available.

General Principle of Cheese-making

In the production of cheese it is necessary to coagulate the cheesemilk to be able to separate the cheese matter e.g. casein from the whey. The milk can be coagulated either by acid treatment or enzyme curdling. In both cases the casein is made insoluble, which leads to the formation of a coherent substances. However, the two coherent coagulated substances (i.e. the cheese material) differ. The coagulate becomes firmer and more elastic when using milk coagulating enzymes, such as rennet (a preparation of rennin which is also called chymosin), in comparison with the coagulate formed when using acids.

Products containing chymosin, which can be isolated from the fourth stomach of calves, have for many years been used for this purpose. Shortage of calf stomachs has in the last decades resulted in the introduction of other milk coagulating enzymes such as bovine pepsin, porcine pepsin as well as microbial enzymes. All these enzymes are characterized by having specificity towards the peptide bond between residue 105 phenylalanine and residue 106 methionine or a bond adjacent to that in kappa-casein. This means that by employing these enzymes in cheese-making, the kappa-casein is split at the junction between para-kappa-casein and a macropeptide moiety called glycomacropeptide (GMP) carrying the negative charges.

When this occurs the macropeptide diffuses into the whey, its stabilizing effect is lost, and the protein micelles can start to aggregate once sufficient amounts of kappa-casein has been hydrolyzed.

This diffusion of macropeptide into the whey means that quite a lot of the milk dry matter is lost into the whey. Whey typically consists of 0.85 % protein, 0.36 % fat and 5.14 % sugars (USDA Table of Standard Reference. U.S. Government Printing Office, 1986). For further elaboration on the enzymatic coagulation of milk see e.g. D. G. Dalgleish in Advanced Dairy Chemistry, Vol 1, ed by P. F. Fox Elsevier, London 1992.

Enzymes and Cheese-making

Enzymes have an important role in the making of cheese and for the flavor, texture, mouth feeling etc. of cheese products.

Certain enzymes are added e.g. to obtain a desired texture. Other enzymes, which are present in the milk raw material, are inactivated e.g. to avoid an undesired flavor.

For instance, the above mentioned milk coagulating enzymes (e.g. rennet) are added at a certain point of time in the cheese-making process to secure the coagulation of the cheese material. Such enzymes are proteases which besides coagulating the milk material further cause a limited degree of breakdown of the milk proteins. This is of importance for the texture and flavor.

Lipases present in the milk will result in liberation of short chain fatty acids from the milk fat triglycerides, which will contribute to a harsh flavor. This can be avoided by heat treating (i.e. usually by pasteurization) the cheesemilk. However, for cheese types such as Danablue and Boerenkaas a harsh flavor is desired.

Lysozyme, which is a glucosidase, is known to be added to the cheese as a preservative. Lysozyme hydrolyzes certain mucopolysaccharides and mucopeptides, which cause lysis of the cell wall of bacteria, such as bacterial cell wall of the genus Clostridium sp.

Transglutaminases are also known to be used for manufacturing milk and milk-like products, such as cheese. Even though the precise action of transglutaminase is not completely understood, it is believed that transglutaminase cross-links proteins in the milk or milk-like product, whereby a lattice or network is generated. This causes gelling of the aqueous phase of such products which can be advantageous.

WO 94/21130 (Novo Nordisk A/S) discloses a method for production of a non-acidified edible gel on milk basis comprising addition of transglutaminase and rennet to milk, followed by a heat treatment. Hereby a functionally and/or organoleptically satisfactory edible gel is obtained, which can be used as mousse, cheese or pudding etc.

From WO 94/21129 (Novo Nordisk A/S) it is known that addition of transglutaminase to milk or milk-like products such as cheese, will lead to products having a pleasant consistency and mouth feeling and exhibit satisfactory organoleptic properties. Further such products can be produced without adding emulsifiers and stabilizers.

WO 93/22930 (Novo Nordisk A/S) describes a method for the production of a milk-like product by adding transglutaminase to a liquid containing milk proteins. The liquid contains $Ca^{++}$, if required, in an amount sufficient for the reaction catalyzed by the transglutaminase, and the pH of the liquid, if required, is adjusted to a value of between 5.5 and 7.5. Hereby a milk-like product which is physically more stable is obtained.

From JP-A-5959151 it appears that modified milk products in gel form can be obtained by addition of transglutaminase to milk.

From JP-A-2276541 it appears that a fibrous, tissue containing protein food can be obtained on the basis of a casein solution, transglutaminase and a milk coagulating enzyme.

JP-A-6030770 concerns a method for protein gelation in a solution or slurry containing 1.0 wt. % or more protein by the action of a new transglutaminase isolated from sea squirt (*Halocynthia roretzi*). It is also mentioned that said transglutaminase can be used for gelling foods such as cheese.

Comments to Prior Art

In conventional processes for making cheese it is a drawback that a considerable amount of protein is lost into the whey, as protein is a valuable component in the cheese product. None of the above mentioned prior art documents solve this problem, as the aim of the preparation methods disclosed in said documents is to stabilize and emulsify milk or milk-like products resulting in a physically improved product. When using one of these disclosed techniques for producing cheese a considerable amount of protein will be lost into the whey, when the whey is separated from the cheese material.

Therefore, it would be desirable to be able to maintain at least some of this above mentioned protein, lost into the whey, in the cheese material when making cheese.

SUMMARY OF THE INVENTION

The object of the present invention is to overcome the above mentioned problem by providing an improved process for making cheese.

The present inventors have surprisingly found that it is possible to make cheese from cheesemilk that has been pretreated with an enzyme capable of maintaining proteins in the cheese material during the cheese-making process. It was found that cheese can be produced in increased yields using this process.

Accordingly, the first aspect of the invention relates to a process for making cheese, comprising:
  a) adding to cheesemilk a transglutaminase, incubating this mixture for a suitable period;
  b) incubating the resulting product with a rennet so as to cause clotting and formation of a coagulate;
  c) separating whey from the coagulate; and
  d) processing the coagulate into cheese.

In another aspect the invention relates to a cheese product produced according to the process of the invention.

Finally, the invention also relates to the use of transglutaminases for maintaining proteins in the cheese material during a cheese-making process.

DETAILED DESCRIPTION OF THE INVENTION

As mentioned above a considerable amount of proteins is lost into the whey when producing cheese using conventional cheese-making processes.

The present inventors have surprisingly found that this loss can be reduced by:
  pre-treating raw materials comprising proteins used in the production of cheese with a transglutaminase, and
  performing a cheese-making process known per se on the pre-treated raw materials.

The "cheese material" is the substances, which after being subjected to the cheese-making process of the invention will constitute the cheese product.

Thus, according to the present invention, there are no particular restrictions on the properties and composition of the raw materials to be used for the production of cheese, and thus, conventional methods of cheese production (beyond the present pre-treating step) may be followed.

Accordingly, the first aspect of the invention is to provide a process for making cheese, comprising:
  a) adding to cheesemilk a transglutaminase, incubating this mixture for a suitable period;
  b) incubating the resulting product with a rennet so as to cause clotting and formation of a coagulate;
  c) separating whey from the coagulate; and
  d) processing the coagulate into cheese.

Transglutaminases are protein-maintaining enzymes capable of increasing the amount of protein left in the coagulated cheese material after incubation with rennet in step b) and further after the separation of whey from the coagulate in step c), in comparison to a corresponding process where the cheesemilk has not been treated with a such enzyme.

Enzymes' capability to maintain an increased amount of protein in the cheesemilk during the cheese-making process can be assayed as described in the Materials and Methods section below.

"Cheesemilk" is the term used for the milk material used for cheese-making.

Cheesemilk may according to the invention originate from ruminants such as cows, sheep, goats, buffalos or camels. Cheesemilk used as the raw material according to the invention can be whole milk, reconstituted milk, concentrated whole milk, low fat milk, cream or a milk product with a fat content from 0% to 50%. In general cheesemilk comprises between 1 % and 6% wt. % protein.

The choice of cheesemilk will normally be dependent on the type of cheese to be made. Most types of cheese can advantageously be prepared by the process of the invention.

If desired, the cheesemilk may be un-pasteurized. However, in most cases the cheesemilk has been pasteurized to improve the quality of the milk. The pasteurization inactivates lipases present in the milk, which is often an advantage, as the presence of lipases will result in a cheese product having a harsh taste. Further, pasteurization kills e.g. coliform bacteria, which may inflict an unpleasant taste upon the cheese and lead to an uncontrolled generation of gas.

According to the present invention, the treatment with a protein-maintaining enzyme involves specifically adding such an enzyme to the raw materials prior to their undergoing conventional cheese-making procedures, and reacting the enzyme with the proteins in the raw material (i.e. cheesemilk).

As mentioned above the protein-maintaining enzyme of the invention is a transglutaminase.

The "transglutaminase" to be used according to the invention can be any transglutaminase, which includes both calcium-dependent and calcium-independent transglutaminases or mixtures of transglutaminases. Transglutaminases are protein-glutamine γ-glutamyltransferases, and have been classified as enzymes having the number E.C. 2.3.2.13 according to Enzyme Nomenclature, Academic Press, Inc., 1992.

Transglutaminases are enzymes capable of catalyzing an acyl transfer reaction, in which a gamma-carboxyamide group of a peptide-bound glutamine residue is the acyl donor. Primary amino groups in a variety of compounds may function as acyl acceptors with the subsequent formation of monosubstituted gamma-amides of peptide-bound glutamic acid. When the epsilon-amino group of a lysine residue in a peptide-chain serves as the acyl acceptor, the transglutaminases form intramolecular or intermolecular gamma-glutamyl-epsilon-lysyl cross-links.

Even though the protein-maintaining action of transglutaminase in cheese-making processes is not completely understood, it is believed that it is a result of the formation of a network between the milk protein molecules.

A wide array of transglutaminases has been identified and isolated from a number of animals and a few plant species. The most widely used animal derived transglutaminase, Factor XIIIa, is a multi-subunit enzyme.

Transglutaminases may, according to the invention, be of e.g. mammalian origin, such as of human or bovine origin, of marine origin, such as derived from sea squirt (*Halocynthia roretzi*), or of microbial origin, such as of bacterial, yeast of filamentous fungus origin, or variants thereof.

In an embodiment of the invention the transglutaminase is Factor XIIIa of human origin.

In another embodiment the transglutaminase is a microbial transglutaminase derived from *Streptomyces lydicus* (former *Streptomyces libani*), or variants thereof. Said microbial transglutaminase is available from Novo Nordisk A/S.

Other suitable microbial transglutaminases have been described, including a transglutaminase from Physarum polycephalum (Klein et al., Journal of Bacteriology, Vol. 174, pages 2599–2605), as well as transglutaminases from *Streptoverticillium mobaraense, Streptoverticillium cinnamoneum*, and *Streptoverticillium griseocarneum* (Motoki et al., U.S. Pat. No. 5,156,956), and from *Streptomyces lavendulae* (Andou et al., U.S. Pat. No. 5,252,469).

Further the transglutaminases described in EP 481 504-A1 (Amano Pharmaceutical Co. LTD.) and WO 96/06931 (Novo Nordisk A/S) are contemplated, which are hereby incorporated by references.

Also transglutaminases derived from the class of fungi-like organisms Oomycetes, preferably from the genus Phytophthora are contemplated. Other relevant Oomycetes transglutaminases are described in PCT/DK96/00031 (Novo Nordisk A/S), which are hereby incorporated by reference.

The amount of transglutaminase to be added is the amount which produces the protein-maintaining effect in the cheese product. It is usually between 0.1–10 mg active enzyme protein per gram of substrate protein, preferably 1–6 mg active enzyme protein per gram of substrate protein.

As cheesemilk in general has a protein content of 1% to 6% proteins, the amount of transglutaminase to be added ranges from about 0.1 g per liter cheesemilk to 60 g per liter cheesemilk, preferably 1 g per liter cheesemilk to 36 g per liter cheesemilk.

It goes without saying, if the transglutaminase is calcium-dependent, the concentration of $Ca^{++}$ is supposed to be of such value that $Ca^{++}$ is able to activate both the transglutaminase and the rennet.

In order to exhibit the enzymatic effect of the protein-maintaining enzyme (added in step a)) the raw materials are incubated with the enzyme for a "suitable period". A suitable period lies within the range of between 10 minutes and 4 hours.

In the specific case of the protein-maintaining enzyme being a transglutaminase the raw material is kept between 10 minutes and 4 hours, preferably between 10 minutes and 3 hours, especially between 10 minutes and 2 hours under conditions which are optimal for transglutaminase, which is at a pH value between 6–7 and at a temperature in the range of 5–60° C., preferably about 40–55° C. In this manner the enzyme reaction may be sufficiently carried out to achieve the desired protein-maintaining effect.

After the pre-treatment with transglutaminase, the transglutaminase may be inactivated by any conventional method which is not harmful to the product, for example by heating the raw materials till about 80° C. for a period of time sufficient to inactivate the transglutaminase. After the eventual inactivation of the transglutaminase the raw materials are treated as described earlier by conventional methods for making cheese.

Before carrying out the enzyme treatment in step a) the milk may be concentrated in various ways such as by evaporation or spray drying, but is preferably concentrated by membrane filtration, i.e. ultrafiltration, in which molecules with a molecular weight of up to 20,000 Dalton are allowed to pass the membrane, optionally with diafiltration before or after ultrafiltration, in which molecules of a molecular weight of up to 500 Dalton are allowed to pass the membrane. For a more detailed description of the ultrafiltration process, see for instance Quist et al., *Beretning fra Statens Mejeriforsøg*, 1986. (Report from the Danish Government's Dairy Test Institution).

A starter culture may be added to the cheesemilk before or simultaneously with the addition of the coagulation inducing enzyme (step b)). The starter culture is a culture of lactic acid bacteria in conventional cheese-making. The culture is added to ferment the lactose present in the cheesemilk and to cause further decomposition of the clotted casein into smaller peptides and free amino acids. This is a result of the starter culture's production of proteases and peptidases. The starter culture may be added in amounts which are conventional for the present purpose, i.e. typically amounts of about 1*E4 to 1*E5 bacteria/g of cheesemilk, and may be added in the form of freeze-dried, frozen or liquid cultures. When the milk employed in the process of the invention is concentrated milk, it is preferred to add the starter culture after concentrating the milk, although this is not an absolute requirement, as the starter culture bacteria will be retained during filtration.

After adding the enzyme which causes clotting in step b) of the process of the invention, e.g. further salting, pressing, and ripening of the curd, may be conducted in the traditional way of producing cheese, e.g. as described by R. Scott, *Cheese-making in Practice*, 2nd Ed., Elsevier, London, 1986.

In a preferred embodiment of the process of the invention the rennet is Rennilase®, and the rennet is used in an amount of between 1 and 30 renneting units/ml activity units/ml of milk or milk-like product.

Another aspect of the invention is to provide a cheese product which has been prepared by the process of the invention.

A final object of the invention relates to the use of transglutaminases for maintaining proteins in the cheesemilk during a cheese-making process. Raw materials encompassed by the term "cheesemilk" are defined above.

Further, transglutaminases which can be used according to this aspect of the invention are described above.

Other features of the invention will become apparent in the following example, which is given to illustrate the invention.

Methods and Materials

Enzymes:

Transglutaminase, Factor XIIIa, 8 mg enzyme protein per gram purified enzyme product (available from Novo Nordisk A/S)

Rennilase® 50 L XL (available from Novo Nordisk DK)

Enzyme Activity

Rennilase® is characterized in the Novo Nordisk product sheet "Cheese-making with Rennilase®" B250g-GB 2500 October 1990 PBz, and the Novo rennet unit is defined in IB 67/3-e. Both these publications are available on request from Novo Nordisk A/S, Novo Allé, DK-2880 Bagsvaerd, Denmark.

Milk

Pasteurized skim milk (available from Mejeriet Enigheden, Lygten, Copenhagen, Denmark)

Protein-maintaining Assay

The capability of an enzyme to maintain an increased amount of proteins in the cheesemilk during cheese-making, can be assayed by:

a) treating skim milk with a suitable amount of the enzyme in question,
b) incubation for a fixed period of time (e.g. 45 minutes),
c) adding the rennet,
d) letting the cheesemilk coagulate,
e) to cut and filter the formed coagulum,
f) separating the whey from the coagulate,
g) collecting the separated whey, and
h) determining the protein content in the whey.

Step a) to h) is repeated except that no enzyme is added in step a).

The capability of the "protein-maintaining enzyme" can then be confirmed or denied by comparing the protein content in the whey of the test using an enzyme and the "blind test.

EXAMPLE

Example 1

Pasteurized skim milk is heated to 32° C. and distributed in beakers with 150 ml in each.

0.4 g transglutaminase enzyme protein per 100 g milk protein is added, and either 0 or 0.1 g $CaCl_2$ per liter. After incubation for 45 minutes, the rennet Rennilase® 50 L XL, is added in the amount of 0.1 g per liter skim milk.

After clotting the coagulum is cut and the whey is collected and filtered through a Whatman CF/C. The content of proteins in the whey is determined as Kjeldahl N*6,28.

The result of the test compared with a "blind test" (i.e. without transglutaminase treatment) is displayed in the table below.

| Sample No. | Transglutaminase g/100 g milk protein | $CaCl_2$ (g/liter cheesemilk) | Protein content in the whey (%) |
|---|---|---|---|
| 1 (blind) | — | 0.0 | 1.001 |
| 2 (blind) | — | 0.1 | 0.954 |
| 3 | 0.4 | 0.0 | 0.928 |
| 4 | 0.4 | 0.1 | 0.909 |

As can be seen from the table a significant amount of protein has been maintained in the cheese material by using transglutaminase.

As will be apparent to those skilled in the art, in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:
1. A process for making cheese, comprising:
   (a) reacting cheesemilk with a transglutaminase wherein the transglutaminase is a Streptomyces or Oomycetes transglutaminase in an amount of 0.1–10 mg
   (b) reacting the product produced in step (a) with a milk coagulating enzyme to produce whey and coagulate;
   (c) separating the whey from the coagulate; and
   (d) processing the coagulate into cheese.
2. The process of claim 1, wherein the milk coagulating enzyme is a rennet.
3. The process of claim 1, wherein the transglutaminase is a *Streptomyces transglutaminase*.
4. The process of claim 3, wherein the transglutaminase is a *Streptomyces lydicus transglutaminase*.
5. The process of claim 1, wherein the transglutaminase is an *Oomycetes transglutaminase*.
6. The process of claim 5, wherein the transglutaminase is a *Phytophthora transglutaminase*.
7. The process of claim 1, wherein the reaction in step (a) takes place for a period of time from 10 minutes to 4 hours.
8. The process of claim 1, wherein the reaction in step (a) takes place at a pH of 5 to 8.
9. The process of claim 1, wherein the incubation in step (a) takes place at a temperature in the range of 5–60° C.
10. A process for making a cheese product, comprising:
   (a) reacting cheesemilk with a transglutaminase wherein the transglutaminase is a Streptomyces or Oomycetes transglutaminase in an amount to maintain the amount of protein in the cheese product;
   (b) reacting the product produced in step (a) with a milk coagulating enzyme to produce whey and coagulate;
   (c) separating the whey from the coagulate; and
   (d) processing the coagulate into the cheese product.
11. The process of claim 10, wherein the milk coagulating enzyme is a rennet.
12. The process of claim 10, wherein the transglutaminase is a Streptomyces transglutaminase.
13. The process of claim 12, wherein the transglutaminase is a Streptomyces lydicus transglutaminase.
14. The process of claim 10, wherein the transglutaminase is an Oomycetes transglutaminase.
15. The process of claim 14, wherein the transglutaminase is a Phytophthora transglutaminase.
16. The process of claim 10, wherein the reaction in step (a) takes place for a period of time from 10 minutes to 4 hours.
17. The process of claim 10, wherein the reaction in step (a) takes place at a pH of 5 to 8.
18. The process of claim 10, wherein the incubation in step (a) takes place at a temperature in the range of 5–60° C.

* * * * *